(12) United States Patent
Chuo et al.

(10) Patent No.: US 8,729,300 B2
(45) Date of Patent: May 20, 2014

(54) METHOD FOR PREPARING METAL SALT OF VALPROIC ACID

(75) Inventors: Wen-Chih Chuo, Taoyuan (TW);
Weichyun Wong, Taoyuan (TW);
Yon-Lian Wu, Taoyuan (TW)

(73) Assignee: Sci Pharmtech, Inc., Taoyuan (TW)

( * ) Notice: Subject to any disclaimer, the term of this patent is extended or adjusted under 35 U.S.C. 154(b) by 276 days.

(21) Appl. No.: 12/539,022

(22) Filed: Aug. 11, 2009

(65) Prior Publication Data

US 2011/0040122 A1    Feb. 17, 2011

(51) Int. Cl.
*C07B 53/00*    (2006.01)

(52) U.S. Cl.
USPC ........................................................ 562/606

(58) Field of Classification Search
None
See application file for complete search history.

(56) References Cited

U.S. PATENT DOCUMENTS

| | | | |
|---|---|---|---|
| 4,127,604 A * | 11/1978 | Chignac et al. | 562/606 |
| 4,558,070 A * | 12/1985 | Bauer et al. | 514/557 |
| 4,895,873 A * | 1/1990 | Schafer | 514/557 |
| 4,988,731 A | 1/1991 | Meade | |
| 5,212,326 A | 5/1993 | Meade | |
| 6,753,349 B1 | 6/2004 | Weh | |
| 2002/0115718 A1* | 8/2002 | Chen et al. | 514/557 |
| 2003/0211148 A1* | 11/2003 | Chen et al. | 424/465 |
| 2005/0276848 A1* | 12/2005 | Podhipleux et al. | 424/468 |
| 2008/0234382 A1* | 9/2008 | Malkar et al. | 514/578 |

FOREIGN PATENT DOCUMENTS

WO    2007004238    *    1/2007

OTHER PUBLICATIONS

Database Caplus Chemical Abstracts Service, Columbus, Ohio, US; Database Accession No. 1985:541455, Abstract of DD 215533, Wuinderlich et al., Nov. 14, 1894.*

* cited by examiner

*Primary Examiner* — Karl J Puttlitz
(74) *Attorney, Agent, or Firm* — Sughrue Mion, PLLC

(57) ABSTRACT

The present invention provides a simple, safe and more efficient process for preparing metal salts of valproic acid. The process includes steps of: (i) mixing valproic acid and a metal hydroxide (either dry solid or aqueous solution) in a drier to form a reaction mixture; and (ii) removing water, which is produced during the step of mixing the valproic acid and the metal hydroxide, from the reaction mixture to obtain the desired metal salts of valproic acid.

6 Claims, No Drawings

METHOD FOR PREPARING METAL SALT OF VALPROIC ACID

BACKGROUND OF THE INVENTION

1. Field of the Invention

The present invention relates to a method for preparing metal salts of valproic acid.

2. Description of Related Art

Valproic acid (VA), which is also known as 2-propylpentanoic acid, 2-propylvaleric acid or di-n-propylacetic acid, and its alkali/alkaline earth salts, e.g. sodium valproate, divalproex sodium and magnesium valproate, have been known to be active pharmaceutical ingredients for treatment of epileptic seizure, convulsion and migraine.

Various methods have been proposed to prepare metal salts of valproic acid. For example, U.S. Pat. Nos. 4,988,731 and 5,212,326 both disclose a process for the preparation of divalproex sodium (Depakote®). In these patents, divalproex sodium, an oligomeric 1:1 compound of valproic acid and sodium valproate, is prepared by dissolving valproic acid and sodium valproate in acetone at 50° C. followed by crystallization at 0° C. However, the disadvantage of the above process is the requirement of using organic solvents (e.g., acetone). Furthermore, the use of hygroscopic material of sodium valproate results in the operation of the process to be more complex. In addition, U.S. Pat. No. 6,753,349 discloses a method for producing valproic acid compounds that involves in the use of alkali metals carbonate/bicarbonate or alkaline earth metals carbonate/bicarbonate. However, it is understood that this process leads to the formation of $CO_2$. Accordingly, the drawback of this patent is the dangerous risk in exhaustion of the undesirable $CO_2$. Also, this additional operation complicates the process for producing valproic acid compounds.

Hence, there is still a need for a simple, safe and more efficient process for preparing metal salts of valproic acid.

SUMMARY OF THE INVENTION

In light of the above-mentioned drawbacks in prior arts, an object of the present invention is to provide a simple, safe and more efficient process for preparing metal salts of valproic acid.

To achieve the aforementioned object, the present invention provides a method for preparing a metal salt of valproic acid without the addition of a solvent as well as the formation of $CO_2$ that is environmentally and economically advantageous. Specifically, the present invention includes the following steps as shown in Reaction Scheme (1) below: (i) mixing valproic acid and a metal hydroxide in a drier to form a reaction mixture; and (2) removing water from the reaction mixture, wherein the water is produced during the step of mixing the valproic acid and the metal hydroxide.

According to the present invention, the metal hydroxide is in a form of a dry solid or an aqueous solution.

Further, the metal salt of the valproic acid obtained from the above Reaction Scheme (1) is represented by the following formula (I):

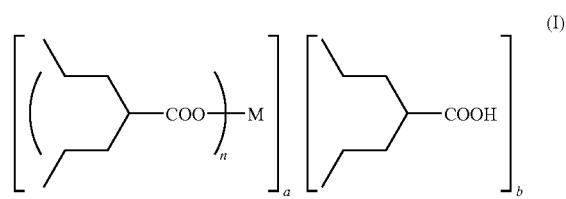

wherein M is an alkali metal when n=1; M is an alkaline earth metal when n=2; a is an integer of from 1 to 10; and b is an integer of from 0 to 10.

According to the present invention, the alkali metal in the formula (I) is Li, Na, K, Rb or Cs, and the alkaline earth metal in the formula (I) is Mg, Ca, Sr or Ba.

DETAILED DESCRIPTION OF PREFERRED EMBODIMENTS

The following illustrative embodiments are provided to illustrate the disclosure of the present invention. These and other advantages and effects can be apparently understood by those skilled in the art after reading the disclosure of this specification. The present invention can also be performed or applied by other different embodiments. The details of the specification may be on the basis of different points and applications, and numerous modifications and variations can be devised without departing from the spirit of the present invention.

EXAMPLES

Example 1

Preparation of Divalproex Sodium

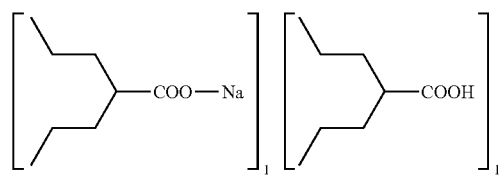

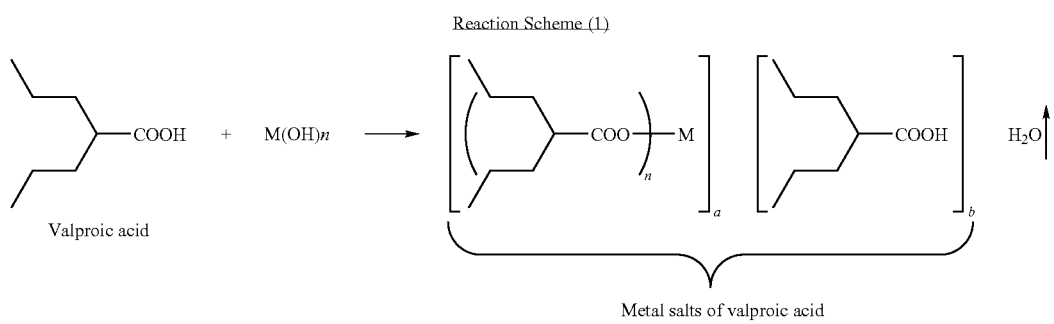

In a 3-L round-bottomed flask was placed valproic acid (144 g, 1 mole) and 40% NaOH aqueous solution (50 g, 0.5 mole). The resulting solution was then put on a rotavaper, applied vacuum, and heated up slowly (e.g., water bath temperature from room temperature to 95° C.) to remove the water. Upon completion of the water removals the reaction mixture was allowed to cool down to room temperature to obtain divalproex sodium (154 g, 100%).

Example 2

Preparation of Sodium Valproate

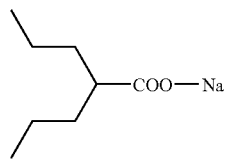

In a 3-L round-bottomed flask was placed valproic acid (144 g, 1 mole) and 40% NaOH aqueous solution (100 g, 1 mole). The resulting solution was then put on a rotavaper, applied vacuum, and heated up slowly (e.g., water bath temperature from room temperature to 95° C.) to remove the water. Upon completion of the water removal, the reaction mixture was allowed to cool down to room temperature to obtain sodium valproate (166 g, 100%).

What is claimed is:

1. A method for preparing a metal salt of valproic acid, comprising:
   mixing valproic acid free from an organic solvent with a metal hydroxide in a drier to form a reaction mixture; and
   removing water from the reaction mixture, wherein the water is produced during the step of mixing the valproic acid and the metal hydroxide,
   wherein the metal salt of the valproic acid is represented by the following formula (I):

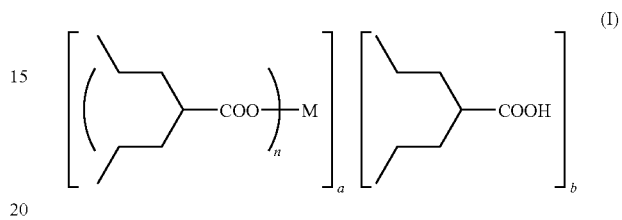

wherein M is an alkali metal when n=1;
M is an alkaline earth metal when n=2; and
a=b=1.

2. The method of claim 1, wherein the metal hydroxide is in a form of a dry solid or an aqueous solution.

3. The method of claim 1, wherein the alkali metal is Li, Na, K, Rb or Cs.

4. The method of claim 1, wherein the alkaline earth metal is Mg, Ca, Sr or Ba.

5. The method of claim 2, wherein the alkali metal is Li, Na, K, Rb or Cs.

6. The method of claim 2, wherein the alkaline earth metal is Mg, Ca, Sr or Ba.

* * * * *